(12) United States Patent
Fujihara et al.

(10) Patent No.: US 10,345,150 B2
(45) Date of Patent: Jul. 9, 2019

(54) TERAHERTZ WAVE SPECTROMETRY SYSTEM

(71) Applicant: Panasonic Intellectual Property Management Co., Ltd., Osaka (JP)

(72) Inventors: Seiji Fujihara, Osaka (JP); Yasuyuki Naito, Osaka (JP); Morio Tomiyama, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/497,181

(22) Filed: Apr. 25, 2017

(65) Prior Publication Data

US 2017/0336261 A1 Nov. 23, 2017

(30) Foreign Application Priority Data

May 19, 2016 (JP) .................... 2016-100080

(51) Int. Cl.
| | | |
|---|---|---|
| G01J 3/42 | (2006.01) | |
| G01J 3/433 | (2006.01) | |
| G01N 21/3581 | (2014.01) | |
| G01J 3/443 | (2006.01) | |
| G01N 21/3563 | (2014.01) | |
| G01N 21/35 | (2014.01) | |
| G01N 21/49 | (2006.01) | |
| G01J 3/28 | (2006.01) | |

(52) U.S. Cl.
CPC .............. *G01J 3/42* (2013.01); *G01J 3/4338* (2013.01); *G01N 21/3581* (2013.01); *G01J 3/443* (2013.01); *G01J 2003/2859* (2013.01); *G01J 2003/421* (2013.01); *G01J 2003/425* (2013.01); *G01N 21/35* (2013.01); *G01N 21/3563* (2013.01); *G01N 21/49* (2013.01)

(58) Field of Classification Search
CPC .......... G01J 3/42; G01J 2003/425; G01J 1/10; G01J 1/18; G01J 2001/4242; G01J 2003/4334; G01J 3/4338; G01N 21/3581; G01N 21/35; G01N 21/45
USPC .................. 250/341.1, 343, 341.8
See application file for complete search history.

(56) References Cited

U.S. PATENT DOCUMENTS 9,279,723 B2 * 3/2016 Roulston ................. G01J 3/108
2006/0255277 A1 11/2006 Cole et al.
(Continued)

FOREIGN PATENT DOCUMENTS

JP 2007-071610 3/2007
JP 2008-151591 A 7/2008
(Continued)

OTHER PUBLICATIONS

Machine Translation of JP 2012-078304A Shibata.*

*Primary Examiner* — David P Porta
*Assistant Examiner* — Carolyn Fin
(74) *Attorney, Agent, or Firm* — McDermott Will & Emery LLP

(57) ABSTRACT

A terahertz wave spectrometry system that is capable of identifying analyzing target molecules contained in an analyte even if the analyte contains water, by activating a water remover to remove water according a comparison of absorption spectrums so that water in the analyte is easily removed without causing the analyzing target molecules to disappear due to decomposition or denaturation.

4 Claims, 14 Drawing Sheets

(56) References Cited

U.S. PATENT DOCUMENTS

2012/0199743 A1 8/2012 Cox et al.
2013/0212904 A1 8/2013 Adachi
2015/0316475 A1 11/2015 Rahman et al.

FOREIGN PATENT DOCUMENTS

| JP | 2010-156544 A | | 7/2010 | | |
|----|---------------|---|--------|---|---|
| JP | 2012-078304 | * | 4/2012 | ............. | B29B 13/06 |
| JP | 2012-078304 A | | 4/2012 | | |
| JP | 2014-194345 A | | 10/2014 | | |

* cited by examiner

TERAHERTZ WAVE SPECTROMETRY SYSTEM

BACKGROUND

1. Technical Field

The present disclosure relates a terahertz wave spectrometry system.

2. Description of the Related Art

Recently, technologies applying electromagnetic waves in the terahertz (THz) frequency region (hereinafter referred to as terahertz waves) have been attracting attention. The terahertz waves are electromagnetic waves in a frequency range from about 0.1 THz to 30 THz. This frequency region is a boundary region between the light region and the radio wave region, and has been an unexplored region until recently. However, with the recent development of the femtosecond laser technologies, non-linear optical technologies, semiconductor device technologies, and so on, fundamental technologies regarding generation, detection and transmission of the terahertz waves have advanced, and applied technologies of the terahertz waves have been developed.

Since characteristic absorption spectrums of various substances can be acquired in the terahertz wave region, application of the absorption spectrums as fingerprint spectrums for molecular discrimination is expected. Particularly, natural vibration frequencies of biologically relevant molecules or organic molecules such as protein, fat and carbohydrate correspond to frequencies in the terahertz frequency region. For this reason, analyses of biologically relevant molecules, studies regarding cells and organic chemistry researches using the terahertz wave spectrometry technology have been attracting attention.

Water is a substance that easily absorbs the terahertz waves. Particularly, the absorbance of the terahertz waves by water increases monotonously as the frequency increases in a range from 0.1 THz to 10 THz. When an analyte contains water, a terahertz wave irradiating the analyte is absorbed mainly by water. In a case where an analyzing target molecule which has a characteristic absorption spectrum with respect to a terahertz wave co-exists with water, the absorption spectrum of water and the absorption spectrum of the analyzing target molecule overlap, so that it is sometimes difficult to distinguish the characteristic absorption spectrum. Because biologically relevant molecules such as protein, fat or carbohydrate often co-exist with water, there is a need for an easy method for detecting and identifying absorption spectrums inherent in such molecules.

PTL1 discloses a means for freezing and heating an analyte by using a phase change means for causing a phase change of the analyte. It is known that water (liquid phase) and ice (solid phase) are different in the absorptance of terahertz waves from each other, and that ice (solid phase) is more transparent to terahertz waves than water (liquid phase). According to the disclosure of PTL1, the analyte is frozen to reduce water (liquid phase), so that the influence of the terahertz wave absorption by water is reduced, and the absorption spectrum of the analyzing target molecule other than water can be easily detected. The frozen samples are heated for exchange and collection of the samples.

CITATION LIST

Patent Literature

PTL 1: Japanese Patent No. 5,164,320
PTL 2: United States Patent Application Publication No. 2006/0255277 A1
PTL 3: United States Patent Application Publication No. 2012/0199743 A1
PTL 4: United States Patent Application Publication No. 2015/0316475 A1

PTL1 discloses such a configuration that a waveguide in which an analyte is placed is provided with a heater so that the analyte can be heated. However, mere heating would possibly cause decomposition or denaturation of the analyzing target molecules of the analyte, and also cause disappearance of the analyzing target molecules existed before measuring. Further, in a case where the analyte is a container such as a dish or the like and analyzation of the surface of the container is required, the container would possibly be deformed or molten if the container is made of a thermally weak material such as a resin or the like.

SUMMARY

One non-limiting and exemplary embodiment provides a system that performs a method of identifying an analyzing target molecule in an analyte, even if the analyte contains water, by easily removing water contained in the analyte without causing the analyzing target molecule in the analyte to disappear due to decomposition or denaturation.

In one general aspect, the techniques disclosed herein feature a terahertz wave spectrometry system comprising:

a terahertz wave emitter for emitting a terahertz wave to irradiate a test substance with the terahertz wave;

a light receiver for receiving an absorbance of a terahertz wave transmitted through or reflected from the test substance; and a water remover for removing water contained in the test substance; and a signal processor, wherein the signal processor, in operative, outputs an irradiation signal instructing the terahertz wave emitter to irradiate the test substance with a terahertz wave having a specified frequency x1;

acquires an intensity of the terahertz wave received by the light receiver;

acquires an absorbance of the terahertz wave which has been transmitted through or reflected from the test substance at the specified frequency x1 on the basis of the intensity of the terahertz wave received by the light receiver; and outputs a drying signal to the water remover to activate the water remover in a case where the absorbance at the specified frequency x1 is equal to or larger than a predetermined value.

The present disclosure provides a system that performs a method of identifying an analyzing target molecule in an analyte, even if the analyte contains water, by easily removing water contained in the analyte, without causing the analyzing target molecule in the analyte to disappear due to decomposition or denaturation.

Additional benefits and advantages of the disclosed embodiments will become apparent from the specification and drawings. The benefits and/or advantages may be individually acquired by the various embodiments and features of the specification and drawings, which need not all be provided in order to acquire one or more of such benefits and/or advantages.

It should be noted that general or specific embodiments may be implemented as a system, a method, an integrated circuit, a computer program, a storage medium, or any selective combination thereof.

DETAILED DESCRIPTION OF THE EMBODIMENTS

First Exemplary Embodiment

Figure 1:
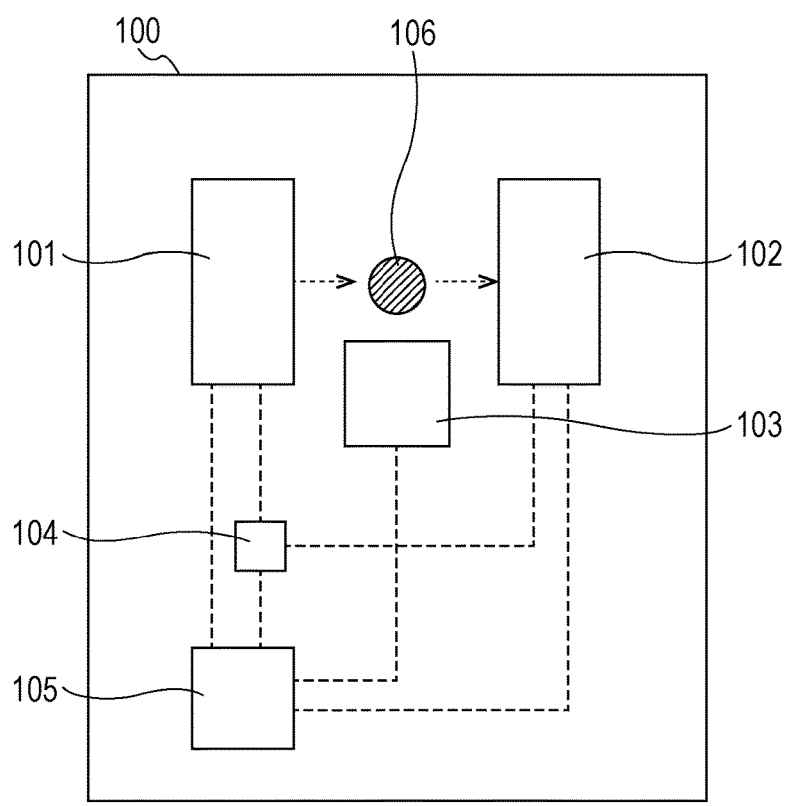
FIG. 1 is a schematic diagram illustrating terahertz wave spectrometry system 100 used for a transmission measurement in accordance with a first exemplary embodiment.

FIG. 1 is a schematic diagram illustrating terahertz wave spectrometry system 100 used for a transmission measurement in accordance with a first exemplary embodiment.

Terahertz wave spectrometry system 100 shown in FIG. 1 has a system configuration for measuring a terahertz wave transmitted through an analyte, and is configured by terahertz wave emitter 101, light receiver 102, water remover 103, first signal processor 104, and second signal processor 105. Analyte 106 is placed on an optical axis between terahertz wave emitter 101 and light receiver 102. Signal processor includes first signal processor 104 and second signal processor 105.

As terahertz wave emitter 101 that generates a terahertz wave, such an terahertz wave emitter may be mainly used that generates a terahertz wave by irradiating a photoconductive element or a non-linear optical crystal with a femtosecond laser pulse having a pulse width in a range from several femtoseconds to several hundred femtoseconds. By using this type of terahertz wave emitter, it is possible to utilize terahertz waves in a frequency range from 0.1 THz to 30 THz.

Analyte 106 is irradiated with the terahertz wave generated by terahertz wave emitter 101, and the terahertz wave transmitted through analyte 106 enters light receiver 102.

Light receivers used as light receiver 102 include a photoconductive element, a pyroelectric light receiver, a bolometer, and the like, which have a wavelength sensitivity in a wide wavelength range.

Also, although not shown in the figure, a light collection optical system configured by a lens or the like may be disposed between terahertz wave emitter 101 and analyte 106. The lens used may be made of a plastic material, such as polyethylene, through which terahertz waves can transmit.

An absorption spectrum of the analyte can be calculated by an arithmetic operation in first signal processor 104 based on an oscillation intensity of a terahertz wave from terahertz wave emitter 101 and a detected intensity of a terahertz wave detected by light receiver 102. An absorbance at each frequency can be known from the calculated absorption spectrum.

The absorption spectrum is disclosed in PTL 2 (see FIG. 6 thereof), PTL 3 (see FIG. 2A thereof), and PTL 4 (see FIG. 19 thereof). It would be easy for a skilled person who has read these patent literatures to acquire the absorption spectrum. See also FIG. 3.

Terahertz wave emitter 101, light receiver 102, first signal processor 104 and water remover 103 are controlled by second signal processor 105.

Figure 2:
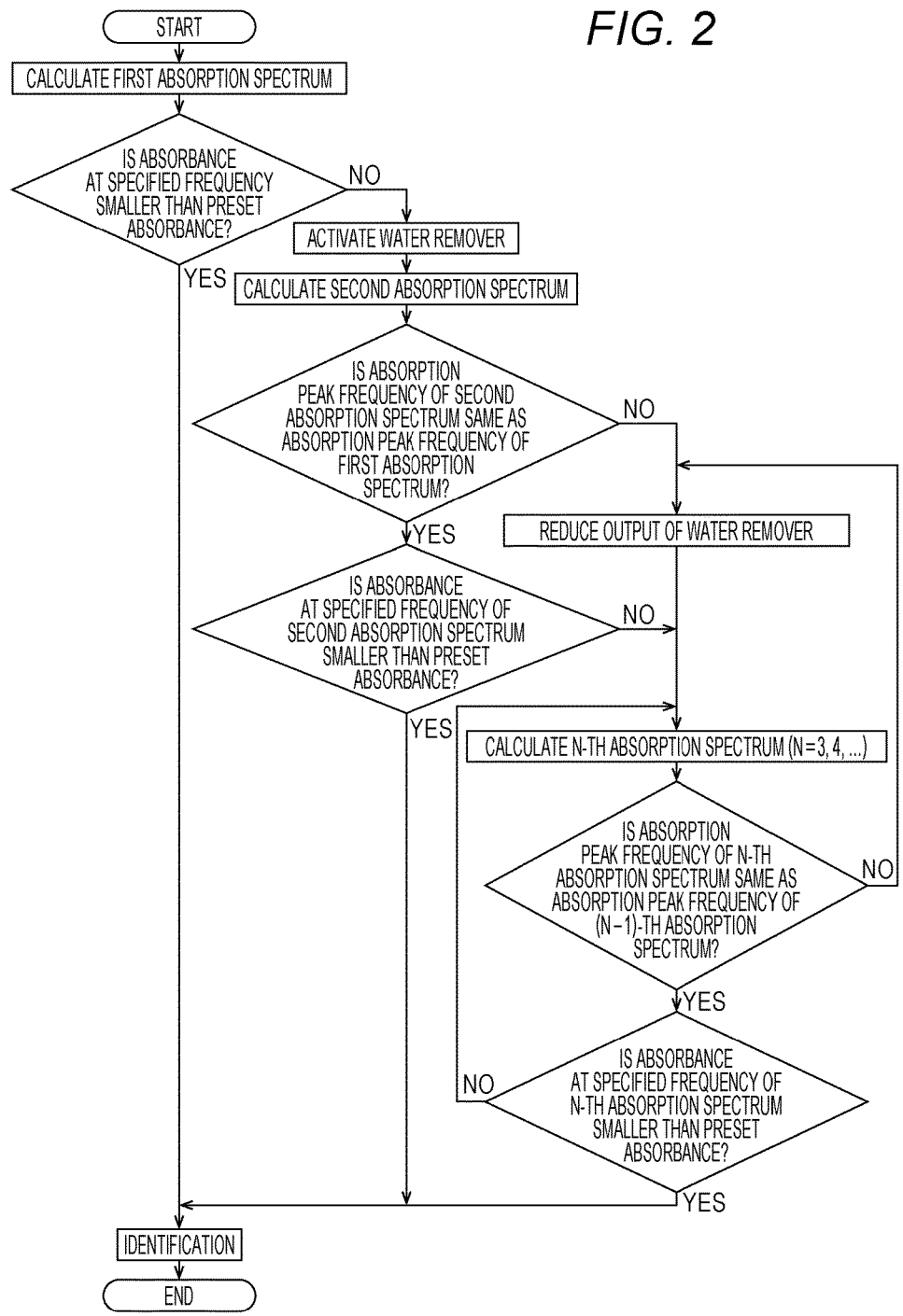
FIG. 2 is a flowchart illustrating operations in accordance with the first exemplary embodiment.

FIG. 2 is a flowchart illustrating operations in accordance with the present exemplary embodiment.

After a measurement start instruction, terahertz wave emitter 101 generates a terahertz wave to irradiate analyte 106 with the generated terahertz wave, and first signal processor 104 performs an arithmetic operation on an intensity of the terahertz wave generated by terahertz wave emitter 101 and an intensity of a terahertz wave detected by light receiver 102 to calculate a first absorption spectrum of analyte 106.

Next, it is determined whether or not an absorbance at a specified frequency of the first absorption spectrum is lower than a preset absorbance. If the absorbance at the specified frequency is lower than the preset absorbance, a step of identifying analyzing target molecules in the analyte is performed, and the measurement is finished. If the absorbance at the specified frequency is equal to or higher than the preset absorbance, water remover 103 is activated.

The specified frequency and the preset absorbance may, for example, be set so as to allow determination of whether or not an absorbance at a frequency of 2.5 THz is lower than 0.5. In this case, water remover 103 may be activated if the absorbance at 2.5 THz is equal to or higher than 0.5.

The specified frequency may be set as a specified frequency range so as to allow determination of, for example, whether or not there is an absorbance lower than 0.5 in a frequency range from 2.0 THz to 2.5 THz. In this case, water remover 103 may be activated if the absorbance is equal to or higher than 0.5 throughout the frequency range from 2.0 THz to 2.5 THz. Depending on the analyzing target molecules exhibiting an absorption peak at 2.5 THz, it is preferable to set the specified frequency as a specified frequency range, and to determine based on the value of the absorbance in the frequency range.

Water remover 103 performs an operation to remove water contained in analyte 106 in response to an activation signal sent from second signal processor 105. In the present exemplary embodiment, a heater is used as water remover 103. However, water remover 103 may be any other means including, for example, heaters such as a warm air heater or an electromagnetic wave heater, a low-humidity environment unit, a vacuum dryer, or the like.

During the operation of water remover 103, terahertz wave emitter 101 again generates a terahertz wave to irradiate analyte 106 with the generated terahertz wave, and then, first signal processor 104 performs an arithmetic operation on an intensity of the terahertz wave generated by terahertz wave emitter 101 and an intensity of a terahertz wave detected by light receiver 102 to calculate a second absorption spectrum of analyte 106.

Next, it is determined whether or not a frequency at an absorption peak in the second absorption spectrum is different from a frequency at an absorption peak in the first absorption spectrum.

To determine the frequency at the absorption peak, it is necessary to determine the absorption peak from the absorption spectrum. A method of determining an absorption peak will hereinafter be described.

A peak may be determined by executing a first-order differentiation of the absorption spectrum to acquire a derivative at each frequency of the absorption spectrum, finding an area in which the derivative once changes from a positive value to zero and thereafter changes to a negative value, and determining as a peak the position where the derivative becomes zero in the area. To acquire frequency values at which first-order differentiation values become zero, it is necessary to execute differentiation operations at a number of frequency values, so that the information processing load becomes large. To avoid the large information processing load, such a method may be used that finds an area in which the derivative changes from a positive value to a negative value, and a point in the area is determined as a peak.

Figure 3:
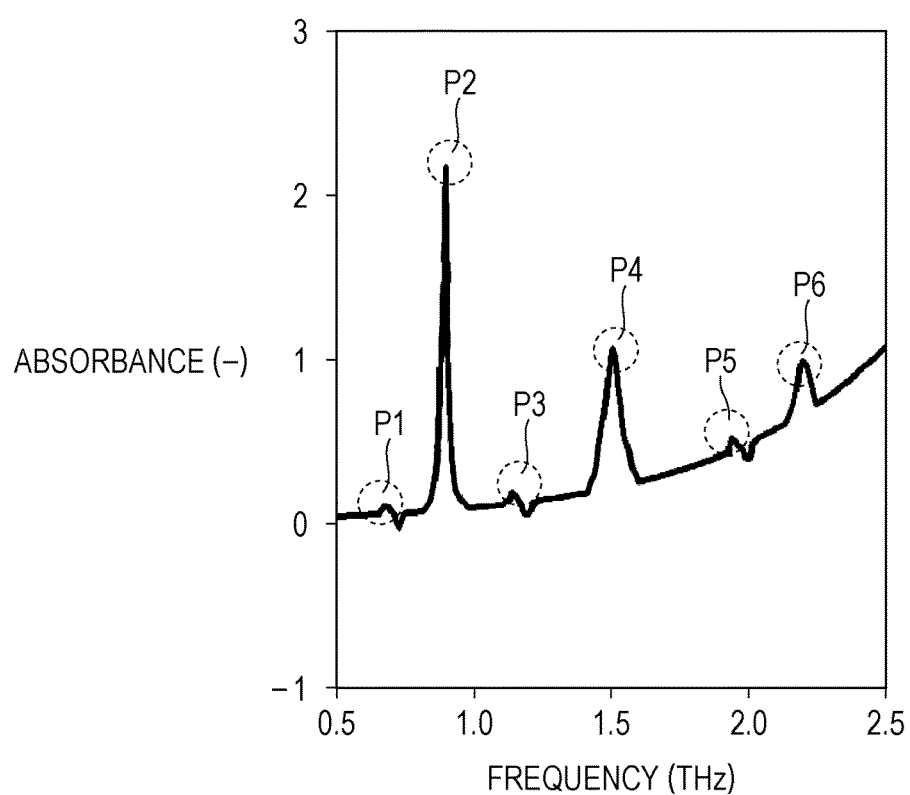
FIG. 3 is a schematic diagram illustrating peaks detected in accordance with the first exemplary embodiment.

FIG. 3 is a schematic diagram illustrating peaks detected from an absorption spectrum. Detected peaks are P1 to P6, each of which is in an area where the derivative of first-order differentiation changes from a negative value to a positive value.

The peaks include those affected by minute concave and convex waveforms caused by noises or the like. A difference in absorbance between each peak of the concave-convex shape and an adjacent bottom is calculated, and a peak at which the difference in absorbance is equal to or larger than a predetermined value is determined as an absorption peak. Here, the bottom is point having a minimum value in a trough part in which the absorbance lands on the baseline after appearance of a crest part in which the absorbance is high. More specifically, the bottom is a point at which the absorbance becomes zero in an area in which the derivative acquired by first-order differentiation once changes from a negative value to zero and thereafter changes to a positive value.

In a case, for example, where a peak is determined as an absorption peak if the difference in absorbance is equal to or larger than 0.2, peaks P2, P4 and P6 in FIG. 3 may be determined as absorption peaks. The value preset as the difference in absorbance may not necessarily be this value, but may be appropriately set considering the sensitivity of the light receiver and conditions of the analyte.

A frequency at an absorption peak of the first absorption spectrum is stored in a memory, and it is determined whether or not a frequency at an absorption peak of the second absorption spectrum is different from the frequency at the absorption peak of the first absorption spectrum.

In a case where the frequency at the absorption peak of the second absorption spectrum is not different from the frequency at the absorption peak of the first absorption spectrum, a step of identifying the analyzing target molecules in the analyte is performed if the absorbance at the specified frequency of the second absorption spectrum is lower than a preset absorbance, and then the measurement is finished. If the absorbance at the specified frequency of the second absorption spectrum is equal to or higher than the preset absorbance, an operation for calculating a third absorption spectrum is performed.

In a case where the frequency at the absorption peak of the second absorption spectrum is different from the frequency at the absorption peak of the first absorption spectrum, an output of water remover 103 is reduced. The change in the frequency at the absorption peak means a possibility that the operation of water remover 103 would cause decomposition or denaturation of the analyzing target molecules detected by the first absorption spectrum and that other molecules would be being produced. If the decomposition or denaturation is progressed in this condition, it is also likely that the analyzing target molecules would disappear and unable to be identified. Accordingly, the output of water remover 103 is reduced to suppress disappearance of the analyzing target molecules due to decomposition.

After the output reduction of water remover 103, an operation for calculating the third absorption spectrum is performed. After calculation of the third absorption spectrum, it is determined whether or not the frequency at the absorption peak of the third absorption spectrum is different from the frequency at the absorption peak of the second absorption spectrum. Depending on the step after the determination, fourth, fifth, . . . , and N-th absorption spectrums are calculated, while it is determined, after each calculation, whether or not the frequency at the absorption peak of the N-th absorption spectrum is different from the frequency at the absorption peak of the (N−1)-th absorption spectrum. The above-described operations are repeated until the absorbance at a specified frequency of the N-th absorption spectrum becomes lower than a preset absorbance. Thereafter, a step of identifying the analyzing target molecules in the analyte is performed, and the measurement is finished.

With the operations as described above, even if the analyte contains water, the analyzing target molecules in the analyte can be identified by easily removing water without causing the analyzing target molecules to disappear.

In a case where the absorbance at the specified frequency does not become lower than the preset absorbance in the N-th absorption spectrum, the measurement may be determined impossible and may be stopped.

In a case where the output of the water remover cannot be reduced any more in the step of reducing the output of the water remover, the measurement may be determined impossible and may be stopped.

Instead of reducing the output of the water remover, the operation of the water remover may be stopped. After the water remover is stopped, the N-th absorption spectrum may be calculated and it is determined, after each calculation, whether or not the frequency at the absorption peak of the N-th absorption spectrum is different from the frequency at the absorption peak of the (N−1)-th absorption spectrum. As another modification, the N-th absorption spectrum may be calculated when the water remover is activated after a lapse of a specified period of time after the water remover had been stopped. The specified period of time may be set to an arbitrary period of time, such as one minute, for example.

A temperature light receiver may be provided for the analyte or the water remover, and the water remover may be operated while measuring the temperature so that the temperature is controlled to be a specified temperature.

The water remover may be operated to produce its output intermittently.

Although the transmission measurement has been described hereinabove, the same effects can be acquired by measuring a reflection intensity of a terahertz wave from the analyte.

Figure 4:
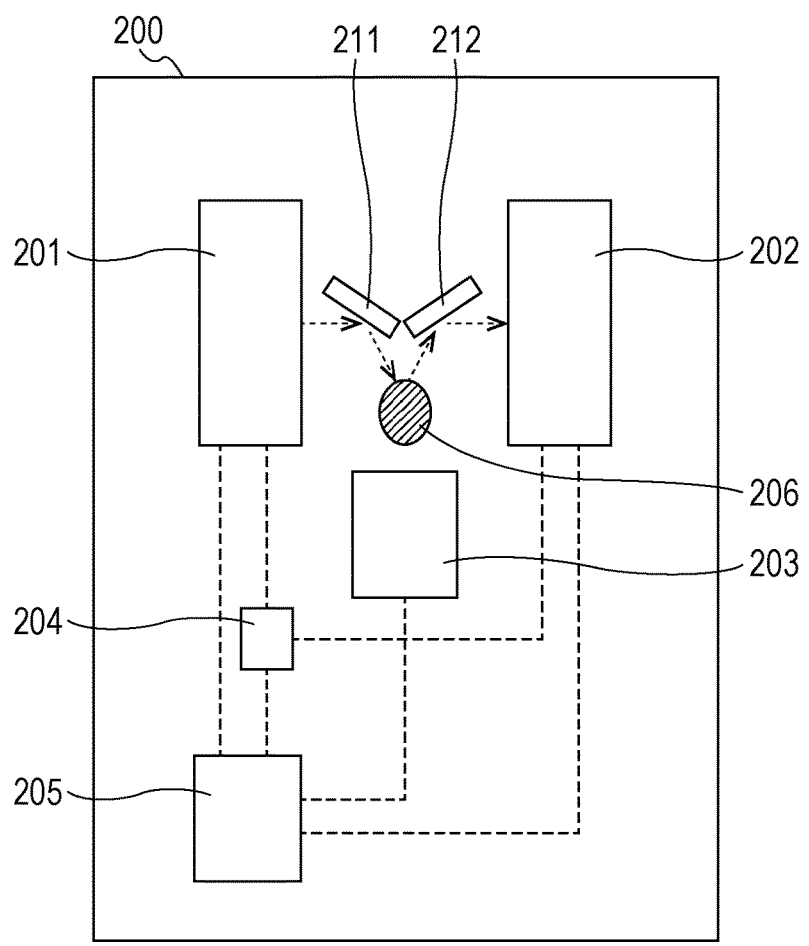
FIG. 4 is a schematic diagram illustrating terahertz wave spectrometry system 200 for reflection measurement in accordance with the first exemplary embodiment.

Hereinafter, description will be made on a case of the reflection measurement. FIG. 4 is a schematic diagram illustrating terahertz wave spectrometry system 200 for reflection measurement. The reflection-type spectrometry system shown in FIG. 4 is configured by terahertz wave emitter 201, light receiver 202, water remover 203, signal processor 204, controller 205, oscillation-side mirror 211, and detection-side mirror 212. A terahertz wave generated from terahertz wave emitter 201 is reflected by oscillation-side mirror 211 to irradiate analyte 206 with the terahertz wave. A terahertz wave reflected from analyte 206 is reflected by detection-side mirror 212 to enter light receiver 202.

Also in the case of the reflection measurement, in the same manner as the transmission measurement, an absorption spectrum of analyte 206 can be calculated in signal processor 204 by an arithmetic operation on an intensity of the terahertz wave generated by terahertz wave emitter 201 and an intensity of the terahertz wave detected by light receiver 202.

Also in the case of the reflection measurement, in the same manner as the transmission measurement, the analyzing target molecule in the analyte can be identified by easily removing water without causing the analyzing target molecules to disappear, by operating water remover 103 according to the acquired absorption spectrum in the manner shown by the flowchart illustrated in FIG. 2.

Second Exemplary Embodiment

A second exemplary embodiment will be described with reference to the schematic diagram of terahertz wave spectrometry system 100 used for a transmission measurement illustrated in FIG. 1, in the same way as the first exemplary embodiment.

In the present exemplary embodiment, a height of an absorption peak is calculated instead of calculating the frequency at the absorption peak, and a reduction of the height of the absorption peak is determined as a start of denaturation or decomposition of the analyzing target molecules. Accordingly, the water remover is controlled when the height of the absorption peak is reduced.

To calculate the height of the absorption peak, peaks and bottoms are detected in the same manner as in the first exemplary embodiment. Then, if a difference between an absorbance at a peak and an absorbance at an adjacent bottom is equal to or larger than a preset value, the peak is determined as an absorption peak, and the adjacent bottom is determined as an absorption bottom.

Figure 5:
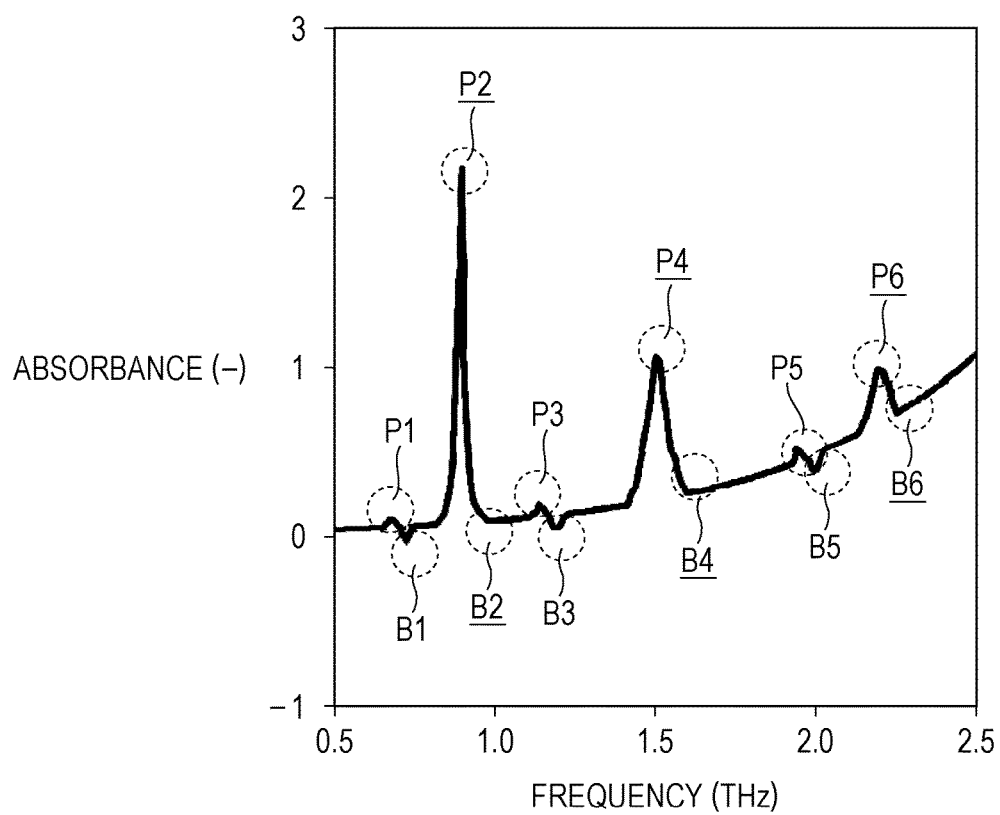
FIG. 5 is a schematic diagram illustrating detected peaks and bottoms and preset absorption peaks and absorption bottoms in accordance with a second exemplary embodiment.

Detected peaks and bottoms, absorption peaks and absorption bottoms are shown in FIG. 5. Detected peaks are P1 to P6, and detected bottoms are B1 to B6. In a case where a peak is determined as an absorption peak if the absorbance difference is equal to or larger than 0.2, absorption peaks are P2, P5 and P6, and absorption bottoms are B2, B5 and B6. The height of the absorption peak can be calculated from the absorbance difference between the absorption peak and the adjacent absorption bottom.

Figure 6:
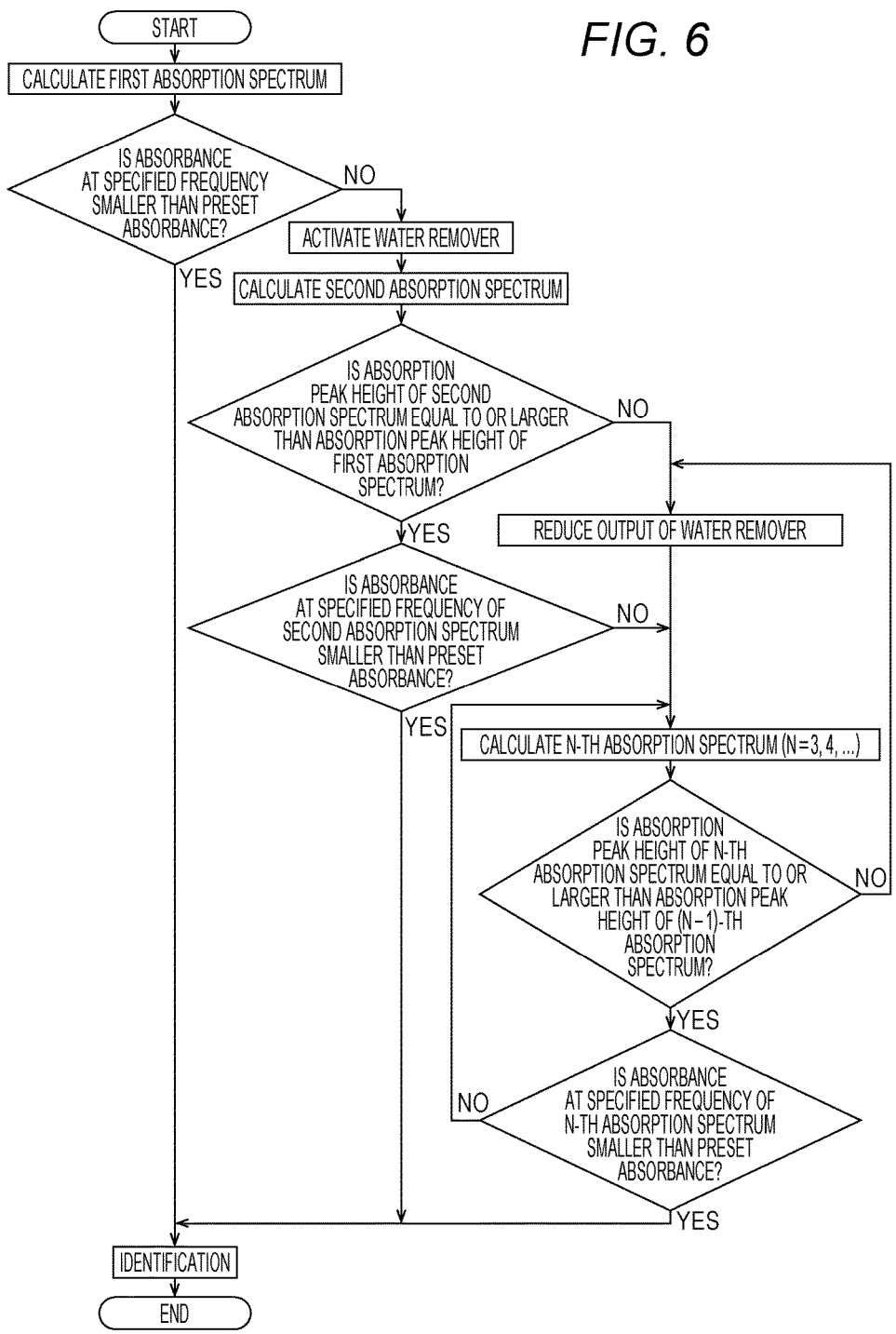
FIG. 6 is a flowchart illustrating operations in accordance with the second exemplary embodiment.

FIG. 6 is a flowchart illustrating operations in accordance with the second exemplary embodiment.

After a measurement start instruction, terahertz wave emitter 101 generates a terahertz wave to irradiate analyte 106 with the generated terahertz wave, and first signal processor 104 performs an arithmetic operation on an intensity of the terahertz wave generated by terahertz wave emitter 101 and an intensity of the terahertz wave detected by light receiver 102 to calculate a first absorption spectrum of analyte 106.

Then, it is determined whether or not an absorbance at a specified frequency of the first absorption spectrum is lower than a preset absorbance. If the absorbance at the specified frequency is lower than the preset absorbance, a step of identifying analyzing target molecules in the analyte is performed, and the measurement is finished. If the absorbance at the specified frequency is equal to or higher than the preset absorbance, water remover 103 is activated.

During the operation of water remover 103, terahertz wave emitter 101 again generates a terahertz wave to irradiate analyte 106 with the generated terahertz wave, and then, first signal processor 104 performs an arithmetic operation on an intensity of the terahertz wave generated by terahertz wave emitter 101 and an intensity of the terahertz wave detected by light receiver 102 to calculate a second absorption spectrum of analyte 106.

Next, it is determined whether or not a height of an absorption peak of the second absorption spectrum is smaller than a height of an absorption peak of the first absorption spectrum. In a case where there are plural absorption peaks, one arbitrary absorption peak may be selected from the plural peaks.

In a case where the height of the absorption peak of the second absorption spectrum is not smaller than the height of the absorption peak of the first absorption spectrum, a step of identifying the analyzing target molecules in the analyte is performed if the absorbance at the specified frequency of the second absorption spectrum is lower than a preset absorbance, and then the measurement is finished. If the absorbance at the specified frequency of the second absorption spectrum is equal to or higher than the preset absorbance, an operation for calculating a third absorption spectrum is performed.

In a case where the height of the absorption peak of the second absorption spectrum is smaller than the height of the absorption peak of the first absorption spectrum, an output of water remover 103 is reduced. The smaller height of the absorption peak indicates a possibility that the operation of water remover 103 may cause denaturation or decomposition of the analyzing target molecules detected by the first absorption spectrum, and that the analyzing target molecules may be decreasing. Accordingly, the output of water remover 103 is reduced to suppress decrease of the analyzing target molecules.

After the output reduction of water remover 103, an operation for calculating the third absorption spectrum is performed. After calculation of the third absorption spectrum, it is determined whether or not the height of the absorption peak of the third absorption spectrum is smaller than the height of the absorption peak of the second absorption spectrum. Depending on the step after the determination, fourth, fifth, . . . , and N-th absorption spectrums are calculated, and at each time, it is determined whether or not the height of the absorption peak of the N-th absorption spectrum is smaller than the height of the absorption peak of the (N−1)-th absorption spectrum. The above-described operations are repeated until the absorbance at a specified frequency of the N-th absorption spectrum becomes lower than a preset absorbance. Thereafter, a step of identifying the analyzing target molecules in the analyte is performed, and then the measurement is finished.

With the operations as described above, even if the analyte contains water, the analyzing target molecules in the analyte can be identified by easily removing water without causing the analyzing target molecules to disappear.

In a case where the absorbance at the specified frequency does not become lower than the preset absorbance in the N-th absorption spectrum, the measurement may be determined impossible and may be stopped.

In a case where the output of the water remover cannot be reduced any more in the step of reducing the output of the water remover, the measurement may be determined impossible and may be stopped.

Instead of reducing the output of the water remover, the operation of the water remover may be stopped. After the water remover is stopped, the N-th absorption spectrum is calculated, and at each time, it is determined whether or not the height of the absorption peak of the N-th absorption spectrum is different from the height of the absorption peak of the (N−1)-th absorption spectrum. As another modification, the N-th absorption spectrum may be calculated when the water remover is activated after a lapse of a specified period of time after the water remover had been stopped. The specified period of time may be set to an arbitrary period of time, such as one minute, for example.

A temperature light receiver may be provided for the analyte or the water remover, and the water remover may be operated while measuring the temperature so that the temperature is controlled to be a specified temperature.

The water remover may be operated to produce its output intermittently.

Although the transmission measurement has been described hereinabove, the same effects can be acquired by measuring a reflection intensity of a terahertz wave from an analyte.

Third Exemplary Embodiment

A third exemplary embodiment will be described with reference to the schematic diagram of terahertz wave spectrometry system 100 used for a transmission measurement illustrated in FIG. 1, in the same way as the second exemplary embodiment.

In the present exemplary embodiment, a state of denaturation or decomposition of the analyzing target molecules is determined by comparing an amount of change of an absorption peak height to an amount of change of an absorbance in another frequency region.

Figure 7:
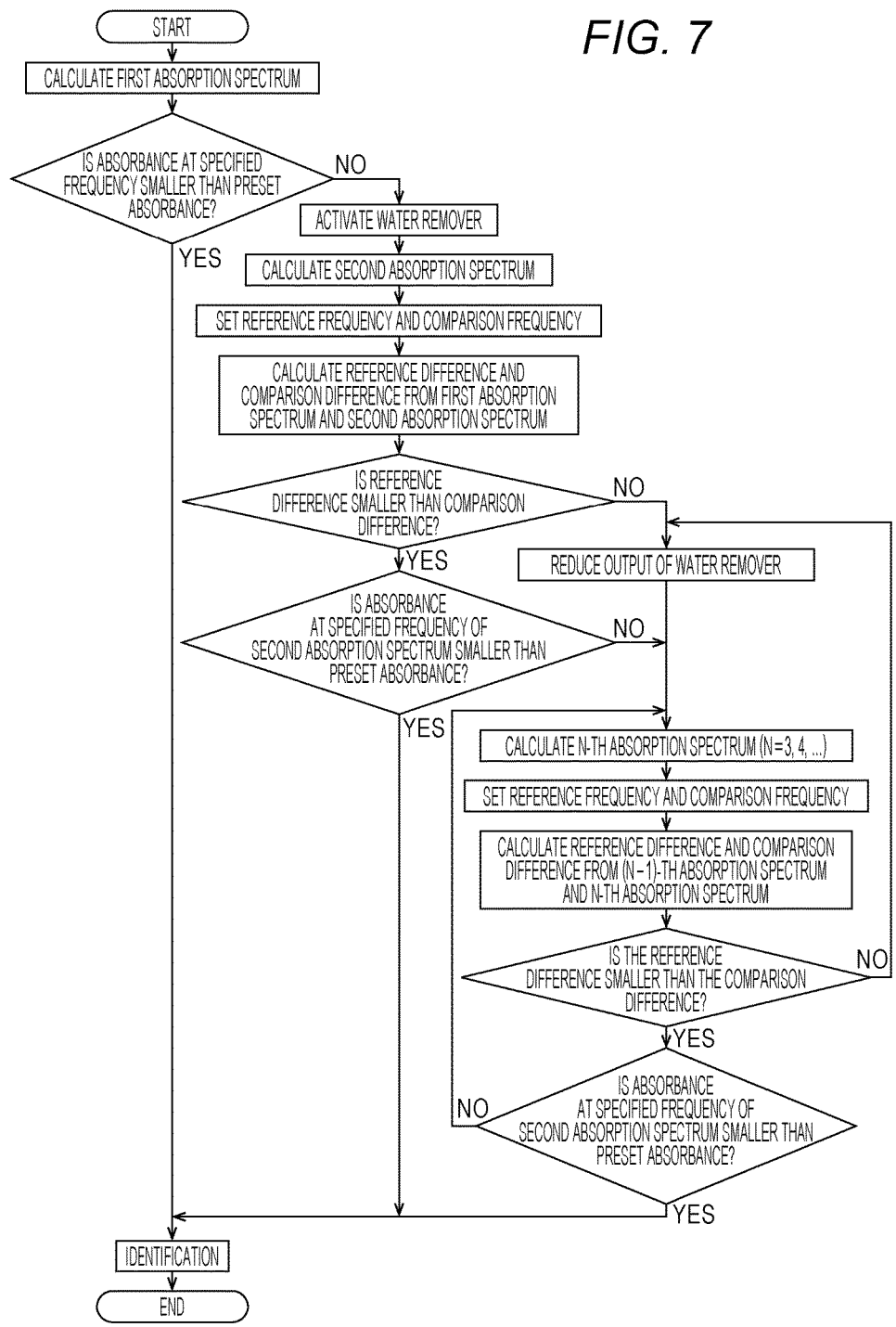
FIG. 7 is a flowchart illustrating operations in accordance with a third exemplary embodiment.

FIG. 7 is a flowchart illustrating operations in accordance with the third exemplary embodiment.

After a measurement start instruction, terahertz wave emitter 101 generates a terahertz wave to irradiate analyte 106 with the generated terahertz wave, and first signal processor 104 performs an arithmetic operation on an intensity of the terahertz wave generated by terahertz wave emitter 101 and an intensity of a terahertz wave detected by light receiver 102 to calculate a first absorption spectrum of analyte 106.

Next, it is determined whether or not an absorbance at a specified frequency of the first absorption spectrum is lower than a preset absorbance. If the absorbance at the specified frequency is lower than the preset absorbance, a step of identifying analyzing target molecules in the analyte is performed, and the measurement is finished. If the absorbance at the specified frequency is equal to or higher than the preset absorbance, water remover 103 is activated.

During the operation of water remover 103, terahertz wave emitter 101 again generates a terahertz wave to irradiate analyte 106 with the generated terahertz wave, and then, first signal processor 104 performs an arithmetic operation on an intensity of the terahertz wave generated by terahertz wave emitter 101 and an intensity of a terahertz wave detected by light receiver 102 to calculate a second absorption spectrum of analyte 106.

Next, a frequency at which an absorption peak of the first absorption spectrum exists is set as a reference frequency. Also, an arbitrary frequency in a frequency region higher than the reference frequency is set as a comparison frequency. The absorption peak may be determined in the same manner as in the second exemplary embodiment.

Next, a reference difference is calculated by subtracting an absorbance at the reference frequency of the second absorption spectrum from an absorbance at the reference frequency of the first absorption spectrum. Also, a comparison difference is calculated by subtracting an absorbance at the comparison frequency of the second absorption spectrum from an absorbance at the comparison frequency of the first absorption spectrum.

Next, it is determined whether or not the reference difference is smaller than the comparison difference.

In a case where the reference difference is smaller than the comparison difference, a step of identifying the analyzing target molecules in the analyte is performed if the absorbance at the specified frequency of the second absorption spectrum is lower than a preset absorbance, and then the measurement is finished. If the absorbance at the specified frequency of the second absorption spectrum is equal to or higher than the preset absorbance, an operation for calculating a third absorption spectrum is performed.

In a case where the reference difference is equal to or larger than the comparison difference, the output of water remover 103 is reduced. The reason for this will be described below.

Usually, the terahertz absorption spectrum of water increases exponentially or quadratically as the frequency increases. Therefore, in a case where the analyte contains water, the overall absorbance is affected by the absorption spectrum of water, and thus tends to increase exponentially or quadratically as the frequency increases. The absorbance at each frequency is proportional to the amount of contained water. Therefore, as water in the analyte is being removed, the absorption spectrum changes such that the difference of absorbance becomes larger in the higher frequency region than in the lower frequency region.

The absorption peaks of the analyzing target molecules appear in a form of being added to the absorption spectrum of water. Therefore, when the water is merely removed, the height of each absorption peak does not change, and the value of absorbance is reduced at the same rate as the reducing rate of the absorbance of water. However, in a case where the quantity of the analyzing target molecules is reduced due to decomposition or denaturation, the height of the absorption peak lowers. In this case, reduction of the absorbance of water and reduction of absorbance due to decrease of the analyzing target molecules are combined. As a result, the reference difference at the reference frequency set at the absorption peak becomes larger than the comparison difference at the comparison frequency set in the higher frequency region than the reference frequency.

In the present exemplary embodiment, by using the above-described phenomenon, it is determined that the absorption peak is decreasing if the reference difference is equal to or larger than the comparison difference in the higher frequency region than the reference frequency, and the output of the water remover is reduced.

After the output reduction of water remover 103, an operation for calculating the third absorption spectrum is performed. After calculation of the third absorption spectrum, the reference difference and the comparison difference are calculated from the third absorption spectrum and the second absorption spectrum, and it is determined whether or not the reference difference is smaller than the comparison difference. Depending on the step after the determination, fourth, fifth, . . . , and N-th absorption spectrums are calculated, and it is determined whether or not the reference difference is smaller than the comparison difference. The above-described operations are repeated until the absorbance at a specified frequency of the N-th absorption spectrum becomes lower than a preset absorbance. Thereafter, a step of identifying the analyzing target molecules in the analyte is performed, and then the measurement is finished.

With the operations as described above, even if the analyte contains water, the analyzing target molecules in the analyte can be identified by easily removing water without causing the analyzing target molecules to disappear.

The comparison frequency may preferably be set so as not to be affected by minute concave-convex shape waveforms caused by noises or the like. Specifically, the comparison frequency may preferably be set higher than the reference frequency by at least 0.1 THz.

In a case where the absorbance at the specified frequency does not become lower than the preset absorbance in the N-th absorption spectrum, the measurement may be determined impossible and may be stopped.

In a case where the output of the water remover cannot be reduced any more in the step of reducing the output of the water remover, the measurement may be determined impossible and may be stopped.

Instead of reducing the output of the water remover, the operation of the water remover may be stopped. After the water remover is stopped, the N-th absorption spectrum is calculated. After the N-th absorption spectrum is calculated, the reference difference and the comparison difference are calculated from the N-th absorption spectrum and the (N−1)-th absorption spectrum, and it is determined whether or not the reference difference is smaller than the comparison difference. As another modification, the N-th absorption spectrum may be calculated when the water remover is activated after a lapse of a specified period of time after the water remover had been stopped. The specified period of time may be set to an arbitrary period of time, such as one minute, for example.

A temperature light receiver may be provided for the analyte or the water remover, and the water remover may be operated while measuring the temperature so that the temperature is controlled to be a specified temperature.

The water remover may be automatically activated to produce its output intermittently.

The reference frequency may not be a frequency at which an absorption peak exists. In this case, the reference difference becoming larger than the comparison difference indicates that the absorbance at the comparison frequency increases. This suggests the possibility that molecules other than the analyzing target molecules are being generated due to decomposition of the analyzing target molecules. Accordingly, the output of the water remover is reduced to suppress decomposition of the analyzing target molecules.

Although the transmission measurement has been described hereinabove, the same effects can be acquired by measuring a reflection intensity of a terahertz wave from an analyte.

Fourth Exemplary Embodiment

Figure 8:
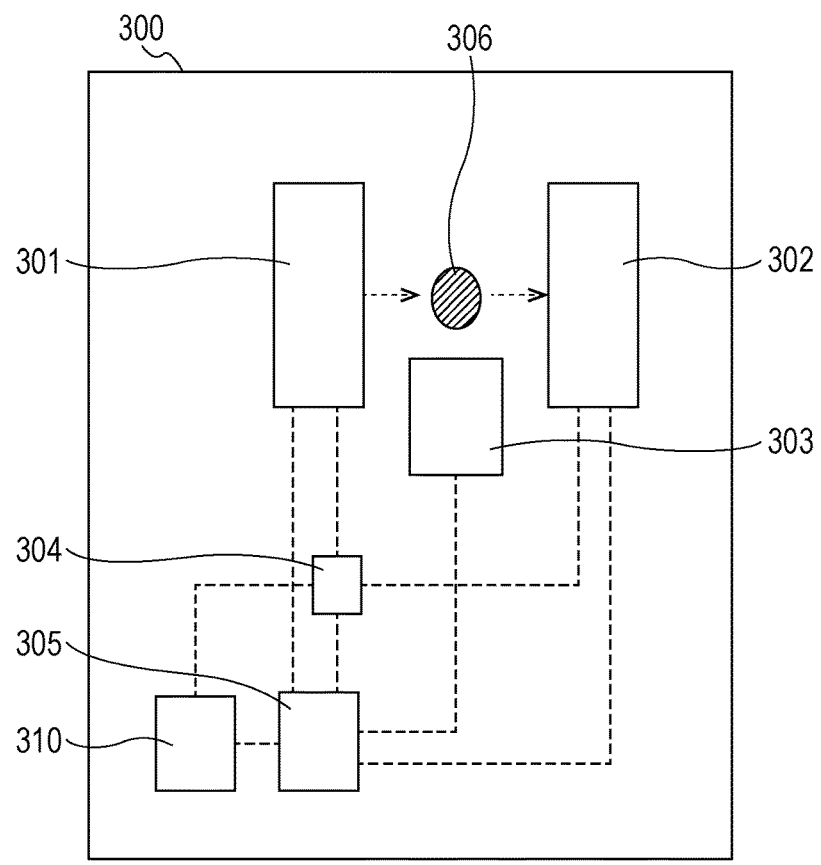
FIG. 8 is a schematic diagram illustrating terahertz wave spectrometry system 300 used for a transmission measurement in accordance with a fourth exemplary embodiment.

FIG. 8 shows a schematic diagram of terahertz wave spectrometry system 300 used for a transmission measurement in accordance with a fourth exemplary embodiment.

Terahertz wave spectrometry system 300 shown in FIG. 8 has a system configuration for measuring a terahertz wave transmitted through an analyte, and is configured by terahertz wave emitter 301, light receiver 302, water remover 303, signal processor 304, and controller 305. Analyte 306 is placed on an optical axis between terahertz wave emitter 301 and light receiver 302. As a difference from the first exemplary embodiment, the present exemplary embodiment is featured by being provided with display unit 310 that is capable of displaying an absorption spectrum of analyte 306.

In the present exemplary embodiment, absorption spectrum of the analyte can be calculated, in the same manner as the first exemplary embodiment, by an arithmetic operation in signal processor 304 based on an oscillation intensity of the terahertz wave from terahertz wave emitter 301 and a detected intensity of a terahertz wave detected by light receiver 302. Also, an absorption spectrum, expressed as an absorbance with respect to frequency, can be calculated in a specified frequency area, and can be stored in a memory.

In the present exemplary embodiment, the N-th absorption spectrum calculated when a step of identifying the analyzing target molecules in the analyte is performed by controller 305 is displayed on display unit 310. Since signal processor 304 can store a plurality of N-th absorption spectrums each calculated when the identifying step is performed, it is possible to display the plurality of N-th absorption spectrums in an overlapped manner on display unit 310. Since the baselines of the absorption spectrums of a plurality of analytes after water removal can be displayed in an overlapped manner, the results can be visually compared. Since the absorption spectrums of analytes different in the amount of water content from one another are usually different from one another in the increase of the overall absorbance as the frequency increases, the first absorption spectrums exhibit different baselines from one another. Therefore, if the displayed baselines acquired as a plurality of measurement results are overlapped, it means that all the results are those acquired after the process of water removal.

It is also possible to display in parallel N-th absorption spectrums calculated when steps of identifying a plurality of analyzing target molecules have been executed.

Although the transmission measurement has been described in the present exemplary embodiment, the same effects can be acquired by measuring a reflection intensity of a terahertz wave from an analyte.

Fifth Exemplary Embodiment

Figure 9:
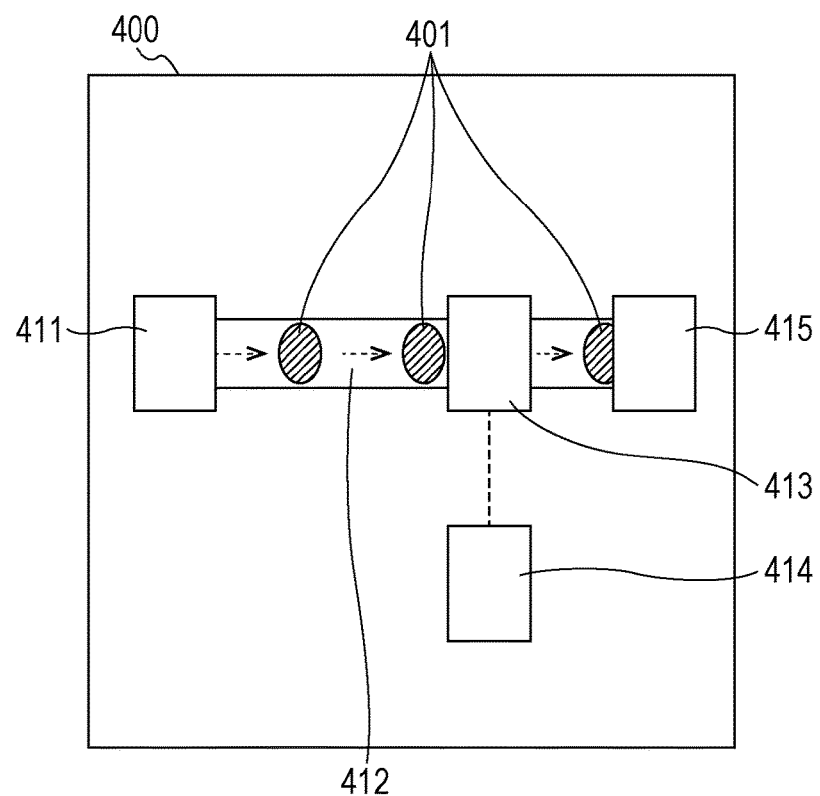
FIG. 9 is a schematic diagram illustrating terahertz wave spectrometry system 400 in accordance with a fourth exemplary embodiment.

FIG. 9 is a schematic diagram illustrating terahertz wave spectrometry apparatus 400 in accordance with a fifth exemplary embodiment. This apparatus functions as an inspection apparatus for determining whether or not organic molecules or bacteria are attached to a surface of a food container.

Food container 401 is transferred from supply apparatus 411 through transfer apparatus 412 to measurement unit 413. Measurement unit 413 is the same in configuration as terahertz wave spectrometry system 100 described in any one of the first, second and third exemplary embodiments.

Terahertz wave spectrometry apparatus 400 is provided with display unit 414 which displays a result of determination, performed in measurement unit 413, of whether or not organic molecules or bacteria were attached to food container 401 at a concentration equal to or higher than a predetermined concentration. Based on the result displayed on display unit 414, a human can determine whether or not organic molecules or bacteria were attached to food container 401 at a concentration equal to or higher than a predetermined concentration. Display unit 414 may display the absorption spectrum.

Food container 401 having been inspected by measurement unit 413 is transferred to collecting apparatus 415. Collecting apparatus 415 may have a configuration of separating food containers 401 to which organic molecules or bacteria are attached and food containers 401 to which organic molecules or bacteria are not attached.

With the configuration as described above, the processes of inspection, separation and collection can be performed uniformly.

In the present exemplary embodiment, even if water exists on the surface of food container 401, it is possible to identify the analyzing target molecules by easily removing the water without causing the analyzing target molecules to disappear.

EXAMPLES

Example 1

Tyrosine was mixed with polyethylene powder, and water was added to the mixture to produce an analyte containing water. Tyrosine was identified from a terahertz wave absorption spectrum of the analyte. Since polyethylene is highly transparent to terahertz waves, and does not affect the absorption spectrum of the analyzing target molecules, polyethylene is used as an admixture of an analyte or as a base material for holding a sample.

The analyte was produced as described below. Polyethylene powder and tyrosine powder were mixed at a weight ratio of 1:1, then water was added to the mixture at a weight ratio of 5% relative to all powder, and the powders and the added water were uniformly mixed to produce an analyte.

A part of the analyte was spread on a sample holder made of a polyethylene plate (10 mm in diameter) so as to have a uniform thickness. The sample holder was configured by surrounding the polyethylene plate by a metal ring so that the diameter of the polyethylene plate within the ring became 10 mm. The step formed by the surface of the polyethylene plate and the metal ring allows the powder to be easily retained on the surface of the polyethylene plate.

Figure 10:
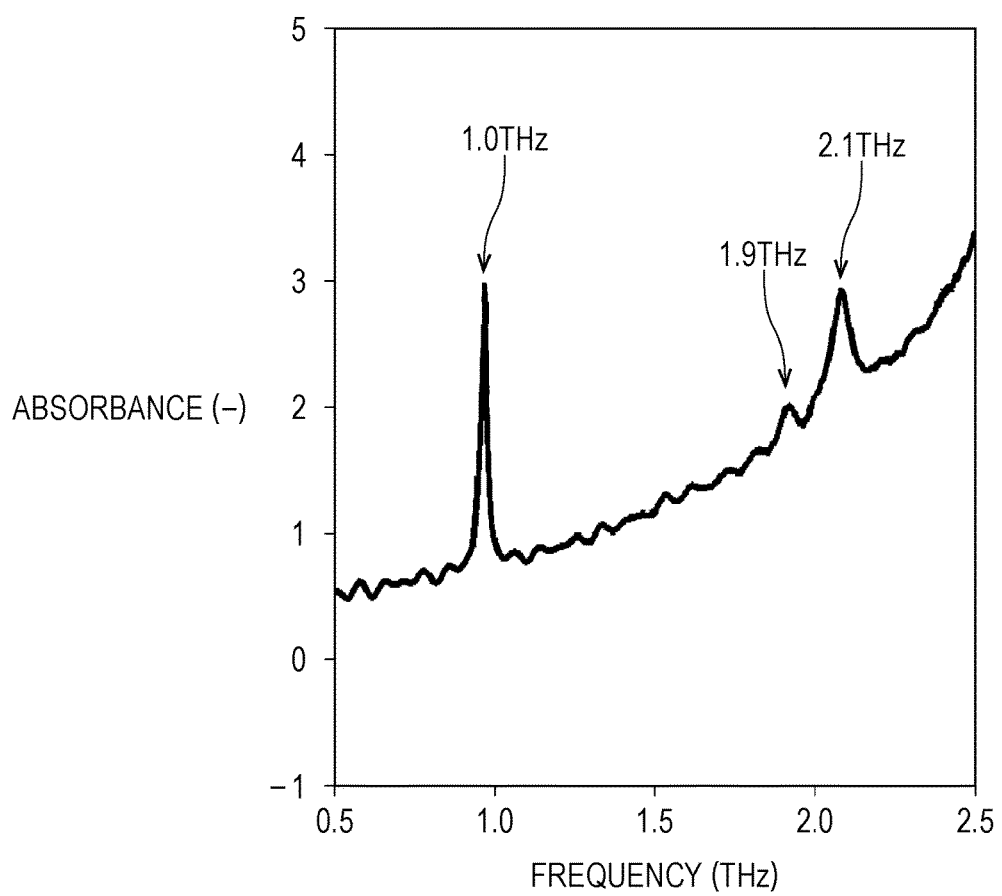
FIG. 10 is a diagram illustrating a first absorption spectrum of an analyte in Example 1.

A first absorption spectrum was calculated by irradiating the analyte spread on the sample holder with a terahertz wave (irradiation spot of 3 mm in diameter) from the above, and detecting a terahertz wave transmitted through the analyte and the sample holder. A result of an absorption spectrum calculated in a frequency range from 0.5 THz to 2.5 THz is shown in FIG. 10. The absorption spectrum showed a tendency that the absorbance as a whole monotonously increased as the frequency increased. Absorption peaks of the first absorption spectrum were calculated, and it was determined that absorption peaks existed at frequencies of 1.0 THz, 1.9 THz and 2.1 THz. To remove the influence of noises, peaks each having an absorbance difference from an adjacent bottom smaller than 0.2 were excluded.

Next, it was determined that an absorbance at a specified frequency was smaller than a preset absorbance. In the present Example, it was determined whether or not the absorbance was smaller than 0.5 in a frequency range from 2.0 THz to 2.5 THz, and it was found that the absorbance in this frequency range was not smaller than 0.5. Accordingly, water in the analyte was removed by energizing a heater provided on the sample holder so that the analyte was heated by radiation heat.

Next, a second absorption spectrum was measured, and frequencies at which absorption peaks existed were determined to be 1.0 THz, 1.9 THz and 2.1 THz. That is, it was confirmed that the absorption peak frequencies of the second absorption spectrum were not different from the absorption peak frequencies of the first absorption spectrum. The above operations were repeated until the absorbance became smaller than 0.5 in the frequency range from 2.0 THz to 2.5 THz, and identification of tyrosine was performed.

Since the water remover was activated while confirming that the absorption peak frequencies of the absorption spectrums did not change by the operations as described above, tyrosine contained in the analyte was successfully identified without causing tyrosine to disappear due to denaturation or decomposition.

Example 2

In the present Example, the water remover was activated while determining whether or not the peak height of the absorption spectrum reduced.

A first absorption spectrum of an analyte produced in the same manner as in Example 1 was calculated by irradiating the analyte with a terahertz wave, and detecting a terahertz wave transmitted through the analyte and the sample holder. A calculated height of an absorption peak of the first absorption spectrum at frequency of 1.0 THz was 2.1.

Since the absorbance was not smaller than 0.5 in the frequency range from 2.0 THz to 2.5 THz, water in the analyte was removed by energizing the heater provided on the sample holder so that the analyte was heated by radiation heat.

Next, a second absorption spectrum was measured, and a calculated height of the absorption peak at frequency of 1.0 THz was 2.1. That is, it was determined that the height of the absorption peak was not reduced from that of the first absorption spectrum.

The above operations were repeated until the absorbance became smaller than 0.5 in the frequency range from 2.0 THz to 2.5 THz, and identification of tyrosine was performed.

Since the water remover was activated while confirming that the height of the absorption peak of the absorption spectrum was not reduced by the operations as described above, tyrosine contained in the analyte was successfully identified without causing tyrosine to disappear due to denaturation or decomposition.

Example 3

In the present Example, the water remover was activated while determining whether or not the reference difference was smaller than the comparison difference.

An analyte was produced as described below. Polyethylene powder and tyrosine powder were mixed at a weight ratio of 1:1, then water was added to the mixture at a weight ratio of 10% relative to all powder, and the powders and the added water were uniformly mixed to produce an analyte. A first absorption spectrum of the analyte was calculated by irradiating the analyte with a terahertz wave, and detecting a terahertz wave transmitted through the analyte and the sample holder.

Since the absorbance in the frequency range from 2.0 THz to 2.5 THz was not smaller than 0.5, water in the analyte was removed by energizing a heater provided on the sample holder so that the analyte was heated by radiation heat.

Figure 11:
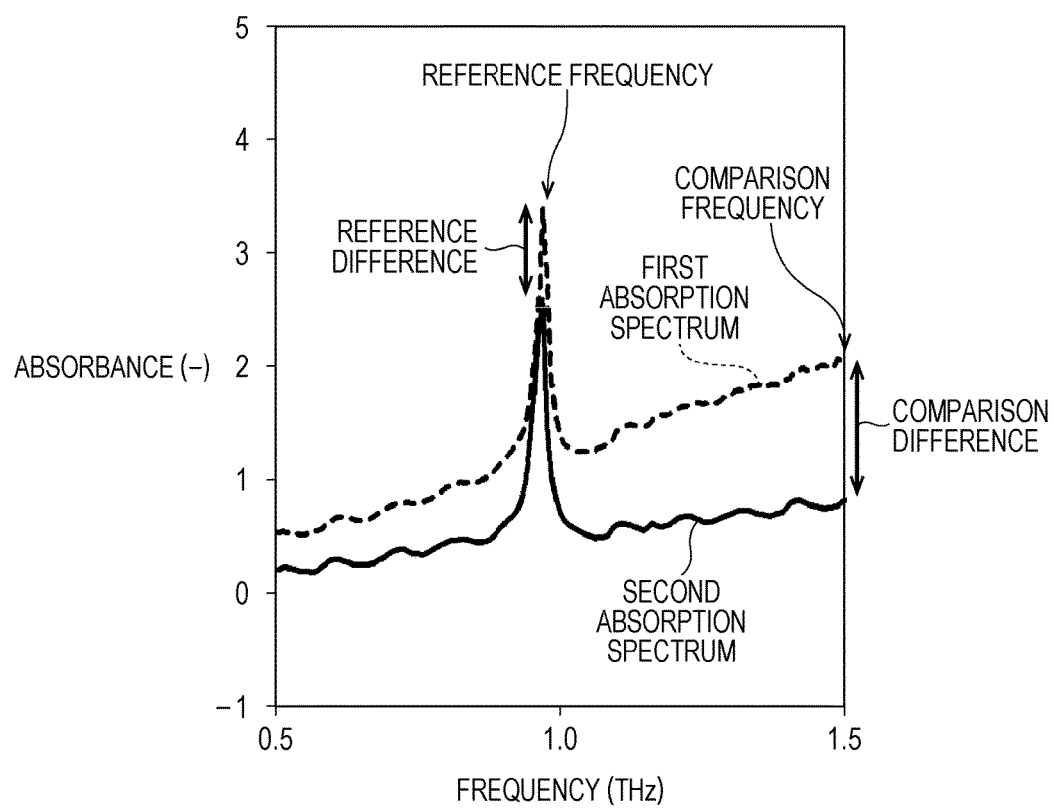
FIG. 11 is a diagram illustrating a first absorption spectrum and a second absorption spectrum of an analyte in Example 3.

Next, a second absorption spectrum was measured. Frequency of 1.0 THz at which an absorption peak existed was set as a reference frequency, and frequency of 1.5 THz, higher than the reference frequency, was set as a comparison frequency. The first absorption spectrum and the second absorption spectrum in the frequency range from 0.5 THz to 1.5 THz are shown in FIG. 11. The first absorption spectrum is indicated by a broken line, and the second absorption spectrum is indicated by a solid line.

The absorbance of the first absorption spectrum at the reference frequency was 3.4, and the absorbance at the comparison frequency was 2.1. The absorbance of the second absorption spectrum at the reference frequency was 2.6, and the absorbance at the comparison frequency was 0.8.

The reference difference was 0.8, and the comparison difference was 1.3. Therefore, the reference difference was smaller than the comparison difference.

While it was determined whether or not the absorbance was smaller than 0.5 in the frequency range from 2.0 THz to 2.5 THz, the above operations were repeated until the absorbance became smaller than 0.5 in this frequency range, and identification of tyrosine was performed.

Since the water remover was activated while confirming that the reference difference was smaller than the comparison difference as described above, tyrosine contained in the analyte was successfully identified without causing tyrosine to disappear due to denaturation or decomposition.

Example 4

In the present Example, two kinds of analytes were measured, and the N-th absorption spectrums used for identification were displayed on the display unit.

The analytes were produced as described below. Polyethylene powder and tyrosine powder were mixed at a weight ratio of 1:1, then water was added to the mixture at a weight ratio of 10% relative to all powder, and the powders and the added water were uniformly mixed to produce sample a. Also, polyethylene powder and tyrosine powder were mixed at a weight ratio of 1:1, then water was added to the mixture at a weight ratio of 5% relative to all powder, and the powders and the added water were uniformly mixed to produce sample b.

Figure 12:
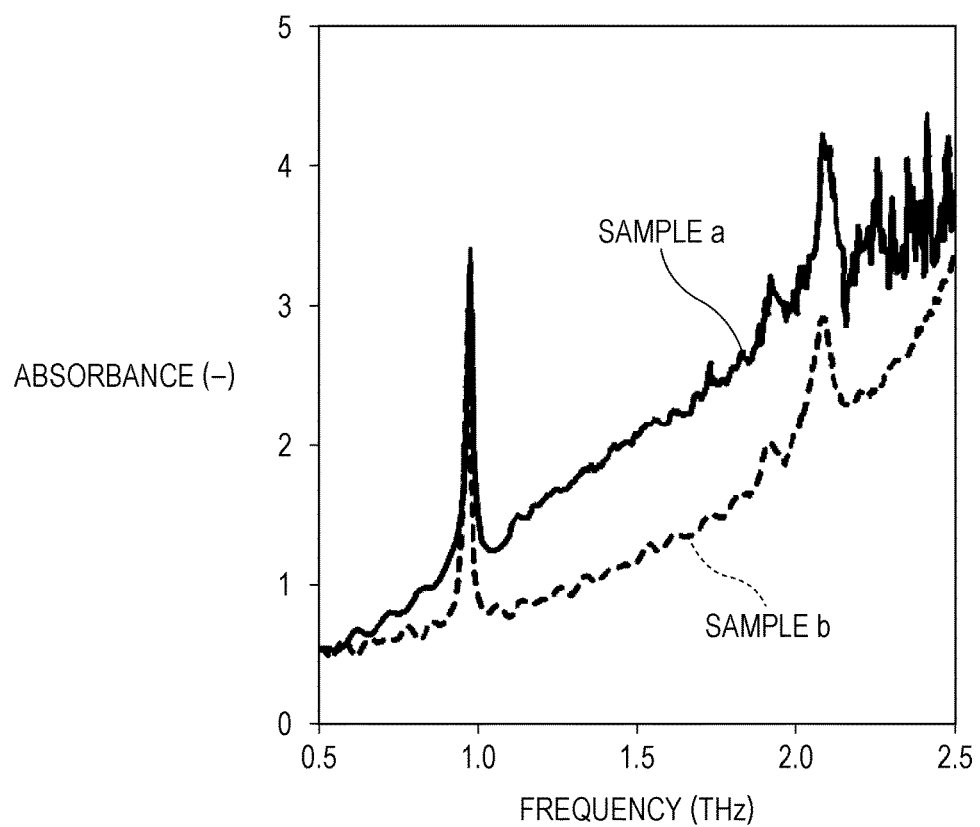
FIG. 12 is a diagram illustrating first absorption spectrums of sample a and sample b in Example 4.

First absorption spectrums of respective samples a and b, or analytes, were calculated by irradiating samples a and b with a terahertz wave, and detecting terahertz waves transmitted through the respective analytes and sample holders. The calculated first absorption spectrums are shown in FIG. 12, in which the first absorption spectrum of sample a is indicated by a solid line, and the first absorption spectrum of sample b is indicated by a broken line.

Water in each of the analytes was removed by energizing the heater provided on the sample holder so that the analyte was heated by radiation heat. Then, a second absorption spectrum of each of the analytes were measured, and the water remover was activated while confirming that the absorption peak frequency was not different from the absorption peak frequency of the first absorption spectrum in the same manner as Example 1.

Figure 13:
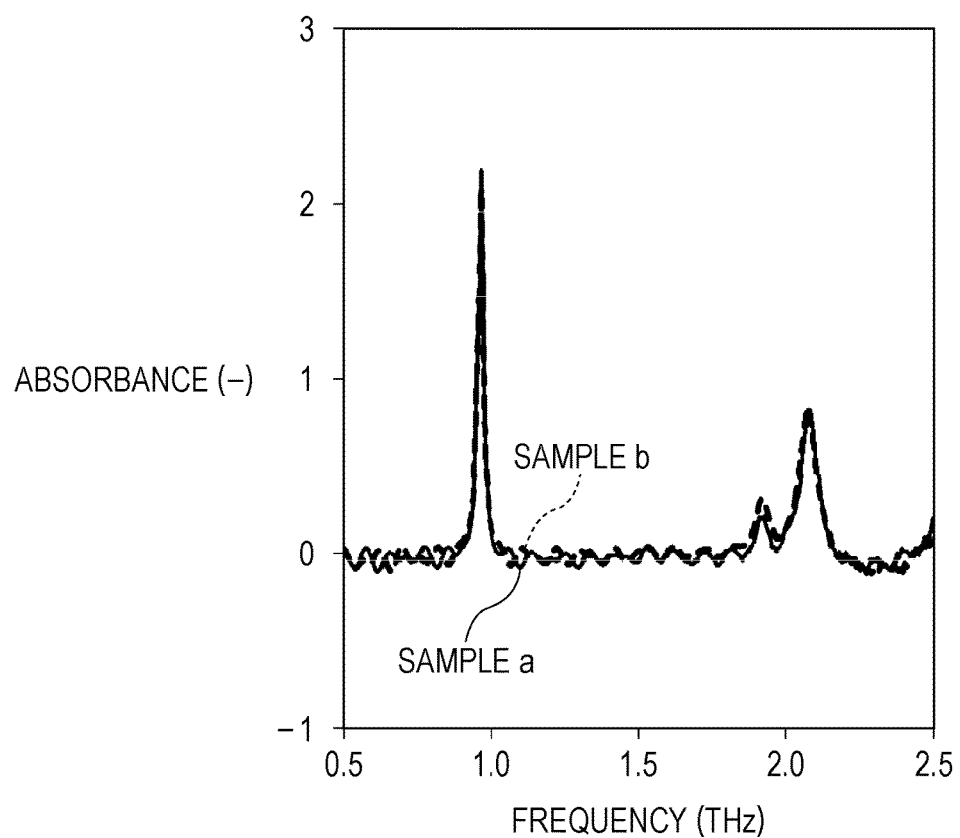
FIG. 13 is a diagram illustrating absorption spectrums used in a step of identifying sample a and sample b in Example 4.

The above-described operations were repeated, and identification of sample a and sample b were performed. The absorption spectrums used for identification are shown in FIG. 13, in which the absorption spectrum of sample a is indicated by a solid line, and the absorption spectrum of sample b is indicated by a broken line.

It was difficult to visually compare the first absorption spectrums of the respective samples a and b, because samples a and b contained different amounts of water from each other. However, by overlapping display of the second absorption spectrums acquired after removing influence of water, it was possible to visually express that samples a and b contained the same amount of tyrosine.

Further, since the water remover was activated while confirming that the absorbance peak frequency of the second absorption spectrum was not different from the absorption peak frequency of the first absorption spectrum, tyrosine contained in the analyte was successfully identified without causing tyrosine to disappear due to denaturation or decomposition.

A first absorption spectrum of an analyte was calculated. A calculated height of an absorption peak of the first absorption spectrum at frequency of 1.0 THz was 2.1.

Since the absorbance was not smaller than 0.5 in the frequency range from 2.0 THz to 2.5 THz, water in the analyte was removed by energizing the heater provided on the sample holder so that the analyte was heated by radiation heat.

Next, a second absorption spectrum was measured, and a calculated height of the absorption peak at frequency of 1.0 THz was 2.1. That is, it was determined that the height of the absorption peak was not reduced from that of the first absorption spectrum.

The above operations were repeated until the absorbance became smaller than 0.5 in the frequency range from 2.0 THz to 2.5 THz, and identification of tyrosine was performed.

Since the water remover was activated while confirming that the height of the absorption peak of the absorption spectrum was not reduced by the operations as described above, tyrosine contained in the analyte was successfully identified without causing tyrosine to disappear due to denaturation or decomposition.

Example 3

In the present Example, the water remover was activated while determining whether or not the reference difference was smaller than the comparison difference.

An analyte was produced as described below. Polyethylene powder and tyrosine powder were mixed at a weight ratio of 1:1, then water was added to the mixture at a weight ratio of 10% relative to all powder, and the powders and the added water were uniformly mixed to produce an analyte. A first absorption spectrum was calculated by irradiating the analyte with a terahertz wave, and detecting a terahertz wave transmitted through the analyte and the sample holder.

Since the absorbance in the frequency range from 2.0 THz to 2.5 THz was not smaller than 0.5, water in the analyte was removed by energizing a heater provided on the sample holder so that the analyte was heated by radiation heat.

Next, a second absorption spectrum was measured. Frequency of 1.0 THz at which an absorption peak existed was set as a reference frequency, and frequency of 1.5 THz, higher than the reference frequency, was set as a comparison frequency. The first absorption spectrum and the second absorption spectrum in the frequency range from 0.5 THz to 1.5 THz are shown in FIG. 11. The first absorption spectrum is indicated by a broken line, and the second absorption spectrum is indicated by a solid line.

The absorbance of the first absorption spectrum at the reference frequency was 3.4, and the absorbance at the comparison frequency was 2.1. The absorbance of the second absorption spectrum at the reference frequency was 2.6, and the absorbance at the comparison frequency was 0.8.

The reference difference was 0.8, and the comparison difference was 1.3. Therefore, the reference difference was smaller than the comparison difference.

While it was determined whether or not the absorbance was smaller than 0.5 in the frequency range from 2.0 THz to 2.5 THz, the above operations were repeated until the absorbance became smaller than 0.5 in this frequency range, and identification of tyrosine was performed.

Since the water remover was activated while confirming that the reference difference was smaller than the comparison difference as described above, tyrosine contained in the analyte was successfully identified without causing tyrosine to disappear due to denaturation or decomposition.

Example 4

In the present Example, two kinds of analytes were measured, and the N-th absorption spectrums used for identification were displayed on the display unit.

The analytes were produced as described below. Polyethylene powder and tyrosine powder were mixed at a weight ratio of 1:1, then water was added to the mixture at a weight ratio of 10% relative to all powder, and the powders and the added water were uniformly mixed to produce sample a. Also, polyethylene powder and tyrosine powder were mixed at a weight ratio of 1:1, then water was added to the mixture at a weight ratio of 5% relative to all powder, and the powders and the added water were uniformly mixed to produce sample b.

First absorption spectrums of respective samples a and b, or analytes, were calculated by irradiating samples a and b with a terahertz wave, and detecting terahertz waves transmitted through the respective analytes and sample holders. The calculated first absorption spectrums are shown in FIG. 12, in which the first absorption spectrum of sample a is indicated by a solid line, and the first absorption spectrum of sample b is indicated by a broken line.

Water in each of the analytes was removed by energizing the heater provided on the sample holder so that the analyte was heated by radiation heat. Then, a second absorption spectrum of each of the analytes were measured, and the water remover was activated while confirming that the absorption peak frequency was not different from the absorption peak frequency of the first absorption spectrum in the same manner as Example 1.

The above-described operations were repeated, and identification of sample a and sample b were performed. The absorption spectrums used for identification are shown in FIG. 13, in which the absorption spectrum of sample a is indicated by a solid line, and the absorption spectrum of sample b is indicated by a broken line.

It was difficult to visually compare the first absorption spectrums of the respective samples a and b, because samples a and b contained different amounts of water from each other. However, by overlapping display of the second absorption spectrums acquired after removing influence of water, it was possible to visually express that samples a and b contained the same amount of tyrosine.

Further, since the water remover was activated while confirming that the absorbance peak frequency of the second absorption spectrum was not different from the absorption peak frequency of the first absorption spectrum, tyrosine contained in the analyte was successfully identified without causing tyrosine to disappear due to denaturation or decomposition.

Comparative Example

In the present Comparative Example, the water remover was activated without determining whether or not the peak height of the absorption spectrum was reduced.

Water was added to powder of phospholipid dimyristoylphosphatidylglycerol (hereinafter referred to as DMPG) at a weight ratio of 10%, and uniformly mixed to produce an analyte.

Figure 14:
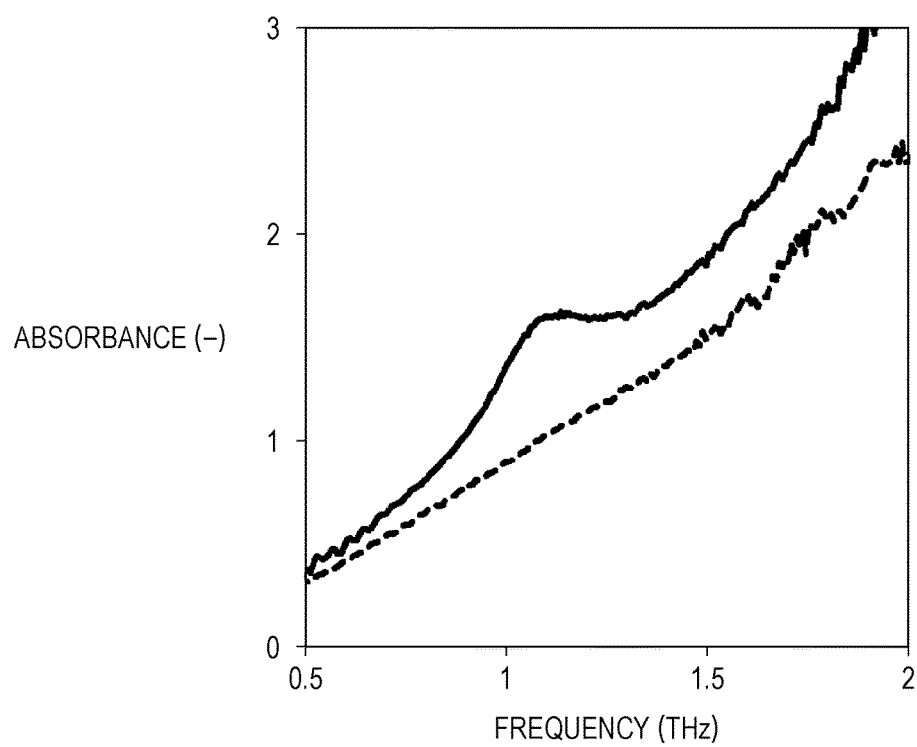
FIG. 14 is a diagram illustrating absorption spectrums in Comparative example.

In the same manner as that in Example 1, a first absorption spectrum of the produced analyte was calculated by irradiating the analyte with a terahertz wave, and detecting a terahertz wave transmitted through the analyte and a sample holder. A result of the absorption spectrum calculated in the frequency range from 0.5 THz to 2.0 THz is shown by a solid line in FIG. 14. An absorption peak exhibiting a maximum value of absorbance was acquired at frequency of 1.1 THz of the absorption spectrum.

In the present Comparative Example, water in the analyte was removed by energizing a heater provided on the sample holder so that the analyte was heated by radiation heat. In the present Comparative Example, a second absorption spectrum was measured after energizing the heater for a long period of time without any control of stopping or reducing the output of the heater. A result is shown by a broken line in FIG. 14. The absorption peak, which had appeared at frequency of 1.1 THz in the first absorption spectrum, was not detected in the second absorption spectrum. Since the water remover (the heater) was activated without determining whether or not the peak height of the absorption spectrum had reduced as described above, DMPG contained in the analyte had disappeared due to denaturation or decomposition. As a result, no absorption peak was detected, or the identification has failed. It is needless to say that DMPG in the analyte did not disappear and was identified in a case where the water remover was activated while determining whether or not the absorption peak height of the absorption spectrum has not been reduced.

The present disclosure provides a terahertz wave spectrometry system. More particularly, the present disclosure provides a terahertz wave spectrometry system that performs a method of identifying an analyzing target molecule contained in an analyte, even if the analyte contains water, by easily removing water contained in the analyte without causing the analyzing target molecule in the analyte to disappear by decomposition or denaturation.

The signal processor (circuitry) may be configured by one or more electronic circuits including a semiconductor device, a semiconductor integrated circuit (IC) or a large scale integration (LSI). The LSI or IC may be integrated on a single chip or may be configured by combining a plurality of chips. For example, functional blocks except for storage elements may be integrated on a single chip. The circuits called LSI or IC herein may be called by another name depending on the degree of integration, and may be what may be called a system LSI, a VLSI (very large scale integration) or a ULSI (ultra large scale integration). Other circuits that may be used for the same purpose include a field programmable gate array (FPGA), which is programmed after being manufactured, or a reconfigurable logic device, which is designed such that it is possible to reconfigure connections within an LSI or to set up circuit blocks within an LSI.

Each of the steps performed in the signal processor may be implemented by a software processing included in a computer. In this case, the software may be stored in one or more non-transitory storage medium such as a ROM, an optical disk, or a hard disk drive, and may be executed by a processor such as a computer so that functions specified in the software can be performed by the processor and peripherals devices. The system or apparatus may have one or more non-transitory storage mediums having stored therein a software, one or more processors, and other necessary hardware devices such as an interface, for example.

REFERENCE SIGNS LIST 100 terahertz wave spectrometry system
101 terahertz wave emitter
102 light receiver
103 water remover
104 signal processor
105 controller
106 analyte
200 terahertz wave spectrometry system
201 terahertz wave emitter
202 light receiver
203 water remover
204 signal processor
205 controller
206 analyte
211 oscillation-side mirror
212 detection-side mirror
300 terahertz wave spectrometry system
301 terahertz wave emitter
302 light receiver
303 water remover
304 signal processor
305 controller
306 analyte
310 display unit
400 terahertz wave spectrometry system
401 food container
411 supply apparatus
412 transfer apparatus
413 measurement unit
414 display unit
415 collecting apparatus

What is claimed is:

1. A terahertz wave spectrometry system comprising:
a terahertz wave emitter configured to emit a terahertz wave to irradiate a test substance with the terahertz wave;
a light receiver configured to receive an absorbance of a terahertz wave transmitted through or reflected from the test substance; and
a water remover configured to remove water contained in the test substance; and
a signal processor, wherein the signal processor is configured to:
output an irradiation signal instructing the terahertz wave emitter to irradiate the test substance with the terahertz wave while increasing or decreasing a frequency x of the terahertz wave;
acquire an intensity of the terahertz wave received by the light receiver;
calculate a function $f1(x)$ of a first absorption spectrum representing the absorbance with respect to the frequency x, on the basis of an intensity of the terahertz wave emitted by the terahertz wave emitter and the intensity of the terahertz wave received by the light receiver;
output a drying signal to the water remover to activate the water remover when an absorbance at a specified frequency x1 of the first absorption spectrum is equal to or larger than a predetermined value;
output an irradiation signal instructing the terahertz wave emitter to irradiate the test substance again with the terahertz wave while increasing or decreasing the frequency x of the terahertz wave;
acquire an intensity of the terahertz wave received by the light receiver again;
calculate a function $f2(x)$ of a second absorption spectrum representing the absorbance with respect to the frequency x, on the basis of an intensity of the terahertz wave emitted again by the terahertz wave emitter and the intensity of the terahertz wave received again by the light receiver; and
output an output reducing signal to the water remover to reduce an output of the water remover when a height of an absorption peak at a frequency x1 of the second absorption spectrum is smaller than a height of an absorption peak at the frequency x1 of the first absorption spectrum.

2. The terahertz wave spectrometry system according to claim 1, wherein the signal processor is further configured to output the output reducing signal to the water remover to reduce the output of the water remover when a frequency at an absorption peak of the second absorption spectrum is different from a frequency at an absorption peak of the first absorption spectrum.

3. The terahertz wave spectrometry system according to claim 1, wherein the signal processor is further configured to output the output reducing signal to the water remover to reduce the output of the water remover when a formula (III) shown below is satisfied:

$$\text{"reference difference"} \geq \text{"comparison difference"} \quad \text{(III)}$$

where:
"reference difference"="a height of an absorption peak at a frequency x1 of the first absorption spectrum"–"a height of an absorption peak at a frequency x1 of the second absorption spectrum";
"comparison difference"="an absorbance at a frequency x2 of the first absorption spectrum"–"an absorbance at a frequency x2 of the second absorption spectrum"; and
x1<x2.

4. A method of removing water contained in a test substance, comprising:
(a) irradiating a test substance with a terahertz wave using a terahertz wave emitter while increasing or decreasing a frequency x of the terahertz wave;
(b) receiving the terahertz wave which has been transmitted through or reflected from the test sample with a light receiver;

(c) calculating a function $f1(x)$ of a first absorption spectrum representing the absorbance with respect to the frequency x, on the basis of an intensity of the terahertz wave emitted by the terahertz wave emitter and the intensity of the terahertz wave received by the light receiver;

(d) determining an absorbance at a specified frequency x1 of the first absorption spectrum is equal to or larger than a predetermined value;

(e) outputting a drying signal to a water remover to activate the water remover based after step (d);

(f) drying the test sample with the activated water remover based on the absorbance at the specified frequency x1 of the first absorption spectrum;

(g) irradiating the test substance with the terahertz wave again using the terahertz wave emitter while increasing or decreasing the frequency x of the terahertz wave;

(h) receiving the terahertz wave which has been transmitted through or reflected from the test sample with a light receiver again;

calculating a function $f2(x)$ of a second absorption spectrum representing the absorbance with respect to the frequency x, on the basis of an intensity of the terahertz wave emitted again by the terahertz wave emitter and the intensity of the terahertz wave received again by the light receiver;

(i) determining that the height of an absorption peak at the frequency x1 of the second absorption spectrum is smaller than a height of an absorption peak at the frequency x1 of the first absorption spectrum; and (j) after step (i) outputting an output reducing signal to the water remover based on the height of the absorption peak at the frequency x1 of the second absorption spectrum.

* * * * *